United States Patent [19]

Duffett

[11] Patent Number: Plant 6,052

[45] Date of Patent: Dec. 1, 1987

[54] CHRYSANTHEMUM PLANT NAMED ZILCON

[75] Inventor: William E. Duffett, Salinas, Calif.

[73] Assignee: Yoder Brothers, Inc., Barberton, Ohio

[21] Appl. No.: 786,002

[22] Filed: Oct. 10, 1985

[51] Int. Cl.[4] ..... A01H 5/00

[52] U.S. Cl. ..... Plt./80

[58] Field of Search ..... Plt./77, 80

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Zilcon, particularly characterized as to uniqueness by the combined characteristics of flat capitulum form; decorative capitulum type; very light red-purple ray floret color; diameter across face of capitulum ranging from 6 to 8 cm. at maturity; uniform nine week photoperiodic flowering response to short days; tall plant height when grown single stem; 25 to 30 cm. peduncles on open, normally terminal sprays; and 13° C. minimum temperature tolerance for initiation and development of flowering buds.

3 Drawing Figures

1

The present invention comprises a new and distinct cultivar of Chrysanthemum botanically known as *Dentrenthema morifolium*, Ramat., previously *Chrysanthemum morifolium*, Ramat., named Zilcon.

Zilcon is a product of a planned breeding program which had the objective of creating new chrysanthemum cultivars having low temperature tolerance for cut spray mum programs with decorative capitulum type, purple ray floret color, eight to nine week flowering response, and the ability to produce commercially acceptable quality in year around programs. Such traits in combination were not present or required improvements in previously available commercial cultivars.

Zilcon, identified as 81861085, was originated from a cross made by William E. Duffett in a controlled environment in Salinas, Calif. in 1980. The pedigree record was inadvertently mislaid. Both parents are unknown.

Zilcon was discovered and selected as one flowering plant within the progeny of the stated cross by William E. Duffett on Nov. 6, 1981 in a controlled environment in Bogota, Colombia.

The first act of asexual reproduction of Zilcon was accomplished when vegetative cuttings were taken from the initial selection in January 1982 in a controlled environment in Bogota, Colombia by a technician working under formulations established and supervised by William E. Duffett.

Horticultural examination of selected units initiated Sept. 21, 1982 has demonstrated that the combination of characteristics as herein disclosed for Zilcon are firmly fixed and are retained through successive generations of asexual reproduction.

Zilcon has not been observed under all possible environmental conditions. The phenotype may vary significantly with variations in environment such as temperature, light intensity and day length. The following observations, measurements and comparisons describe plants grown in Salinas, Calif. and Bogota, Colombia under greenhouse conditions which approximate those generally used there in commercial practice.

The following traits have been repeatedly observed and are determined to be basic characteristics of Zilcon which in combination distinguish this Chrysanthemum as a new and distinct cultivar:

2

(1) Flat capitulum form.
(2) Decorative capitulum type.
(3) Very light red purple ray floret color.
(4) Diameter across face of capitulum ranging from 6 to 8 cm. at maturity.
(5) Uniform nine week photoperiodic flowering response to short days.
(6) Long peduncle length, ranging from 25 to 30 cm.
(7) Tall plant height, requiring one long day week prior to short days to attain a flowered plant height of 95 to 110 cm. for year around flowerings.
(8) Low temperature tolerance of 13° C. for initiation and development when grown in single stem cut spray programs with a continuous dark period of 12 to 13 hours.

The accompanying photographic drawings show typical inflorescence and leaf characteristics of Zilcon, with the colors being as nearly true as possible with illustrations of this type.

Sheet 1 is a color photograph of Zilcon grown as a single stem cut spray.

Sheet 2 is a black and white photograph of three views of the inflorescence of Zilcon.

Sheet 3 is a black and white photograph showing the upper and under sides of the leaves of Zilcon at three stages of development (mature, intermediate and immature).

Of the commercial cultivars known to the present inventor, the most similar in comparison to Zilcon is Beloved, disclosed in U.S. Plant Pat. No. 3,741. Reference is made to attached Chart A which compares certain characteristics of Zilcon to those same characteristics of Beloved.

Similar traits are type, form, capitulum diameter, response and plant height. Zilcon develops a much lighter color than Beloved, longer peduncles, and displays far superior tolerance of low temperature for initiation and development of buds.

In the following description, color references are made to The Royal Horticultural Society Colour Chart. The color values were determined on plant material grown in Salinas, Calif. on July 18, 1985.

Classification:

*Botanical.*—*Dentrenthema morifolium,* Ramat., cv Zilcon.

*Commercial.*—Decorative cut spray mum.

I. INFLORESCENCE

A. Capitulum:

*Form.*—Flat.

*Type.*—Decorative.

*Diameter across face.*—6 to 8 cm.

B. Corolla of ray florets:

*Color (general tonality from a distance of three meters).*—Very light red-purple.

*Color (upper surface).*—155D tinged with 62D.

*Color (under surface).*—155D very slightly tinged with 62D.

*Shape.*—Oblong; broad; rounded tip.

C. Corolla of disc florets:

*Color (mature).*—151D.

*Color (immature).*—151B.

D. Reproductive organs:

*Androecium.*—Present disc florets only; scant pollen.

*Gynoecium.*—Present both ray and disc florets.

II. PLANT

A. General appearance:

*Height.*—Tall; 95 to 110 cm. as a flowering plant from a rooted cutting, with seven long days for year around flowerings and maintaining a minimum nightly 12 hour continuous dark period.

B. Foliage:

*Color (upper surface).*—147A.

*Color (under surface).*—147B.

*Shape.*—Deeply lobed and coarsely serrated.

CHART A

COMPARISON OF ZILCON AND BELOVED

| CULTIVAR | RAY FLORET COLOR | CAPITULUM FORM AND TYPE | SPRAY FORMATION | DIAMETER ACROSS FACE OF CAPITULUM |
|---|---|---|---|---|
| ZILCON | VERY LIGHT RED-PURPLE | FLAT DECORATIVE | 25 to 30 cm. PENDUNCLES | 6 to 8 cm. |
| BELOVED | LAVENDER | FLAT DECORATIVE | 15 to 25 cm. PENDUNCLES | 6.5 to 8 cm. |

| CULTIVAR | PLANT HEIGHT | FLOWERING RESPONSE PERIOD | LOW TEMPERATURE TOLERANCE |
|---|---|---|---|
| ZILCON | TALL 95 to 110 cm. | NINE WEEKS | 13° C. |
| BELOVED | TALL 92 to 108 cm. | NINE WEEKS | INTOLERANT |

COMPARISONS MADE OF PLANTS GROWN AS SINGLE STEM CUT SPRAY MUMS WITH 7 LONG DAYS IN BOGOTA, COLOMBIA

I claim:

1. A new and distinct plant of *Dentrenthema morifolium,* Ramat., named Zilcon, as described and illustrated, and particularly characterized as to uniqueness by the combined characteristics of flat capitulum form; decorative capitulum type; very light red-purple ray floret color; diameter across face of capitulum ranging from 6 to 8 cm. at maturity; uniform nine week flowering response; tall plant height when grown single stem; 25 to 30 cm. peduncles on open, normally terminal sprays; and 13° C. minimum temperature tolerance for initiation and development of flowering buds.

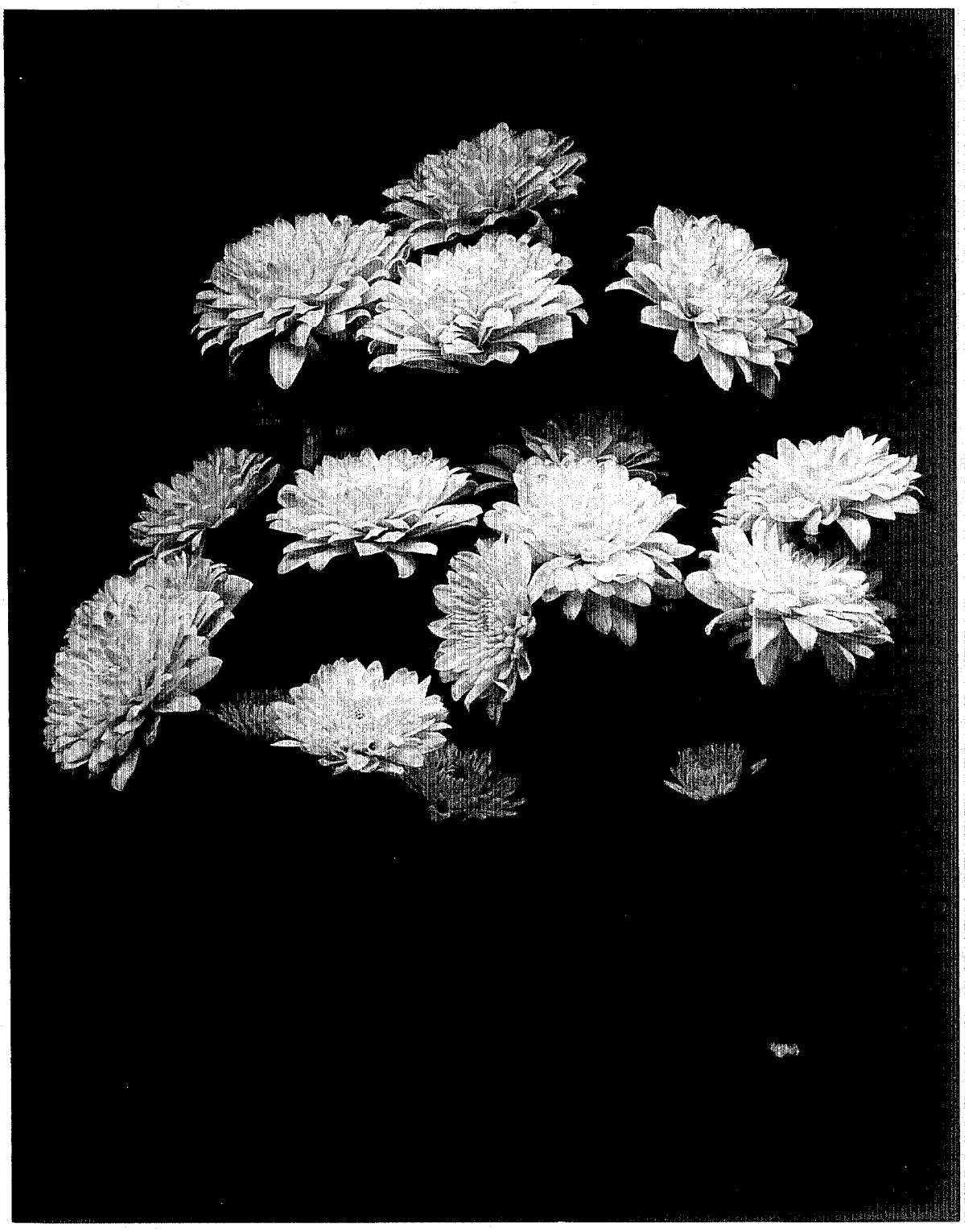

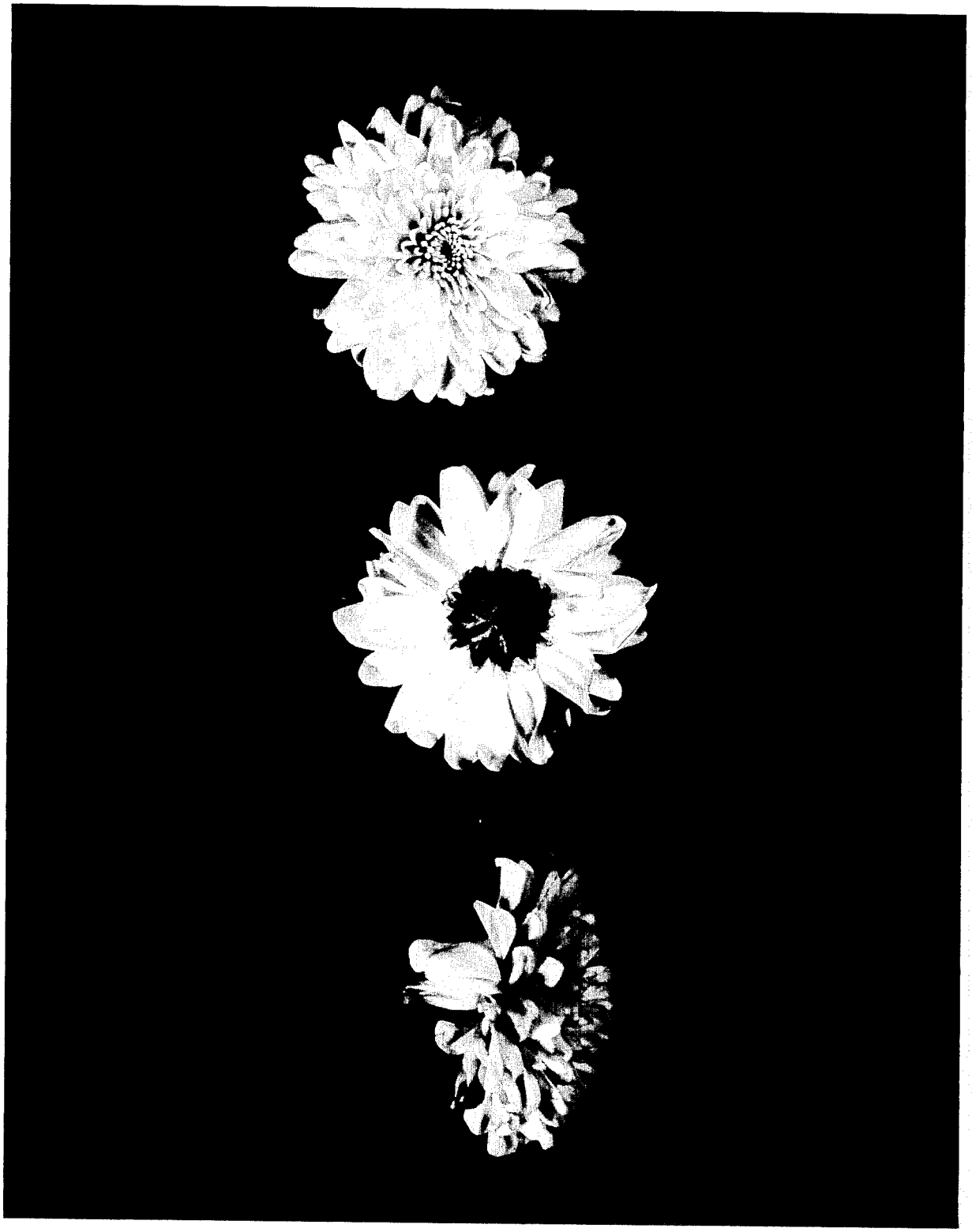

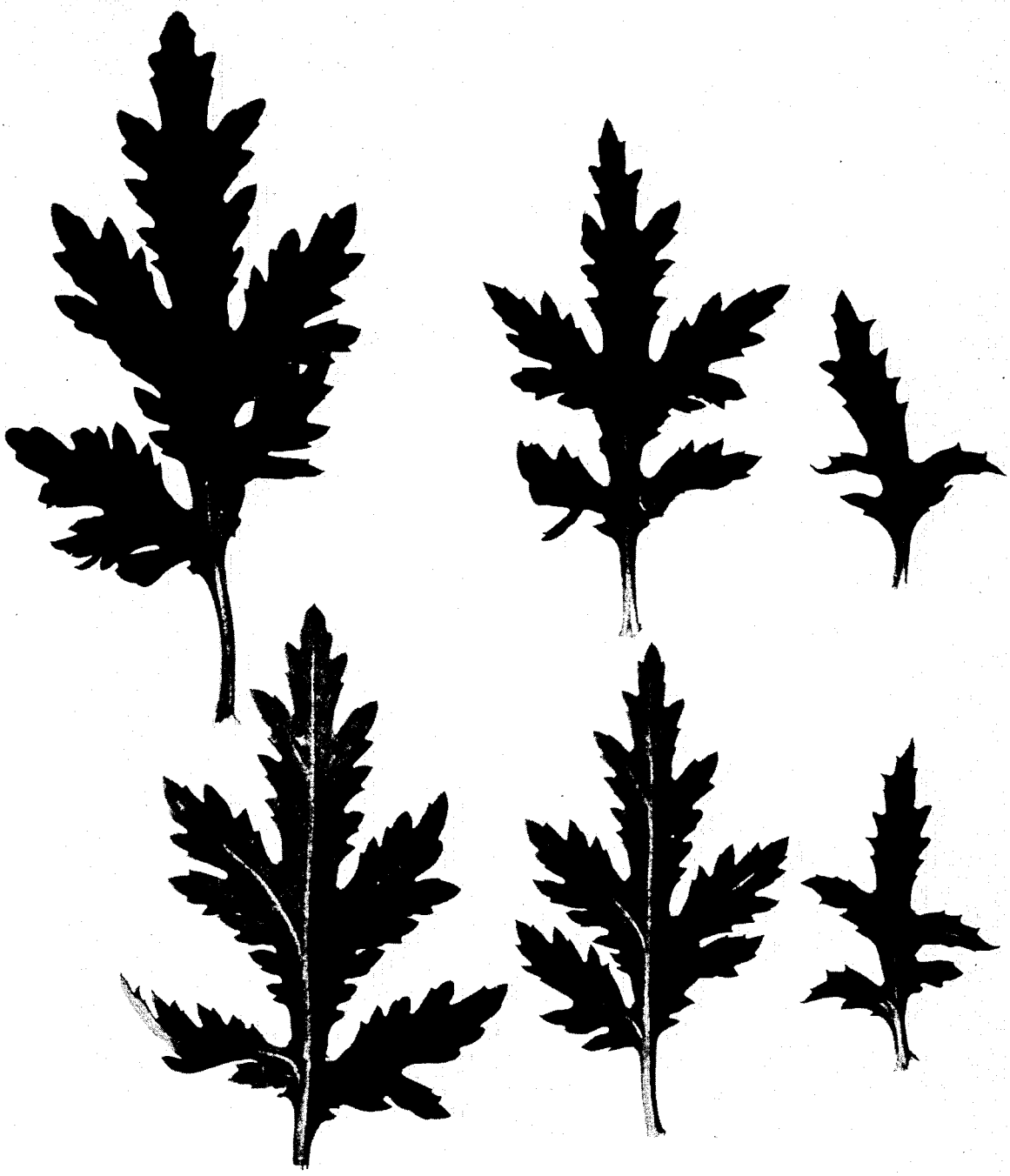

* * * * *